United States Patent [19]
Cook, Jr.

[11] Patent Number: 4,857,853
[45] Date of Patent: Aug. 15, 1989

[54] ON-LINE ELECTROSTATIC DEFECT DETECTOR FOR POLYESTER BASE

[75] Inventor: Henry W. Cook, Jr., Brevard, N.C.

[73] Assignee: E. I. Du Pont de Nemours and Company, Wilmington, Del.

[21] Appl. No.: 76,726

[22] Filed: Jul. 23, 1987

[51] Int. Cl.<sup>4</sup> .............. G01N 27/61; G01R 5/28
[52] U.S. Cl. ........................... 324/456; 324/72; 324/452
[58] Field of Search .......... 324/71.1, 72, 72.5, 324/452, 454–457, 554, 558; 73/159, 150 R

[56] References Cited

U.S. PATENT DOCUMENTS

| | | | |
|---|---|---|---|
| 3,358,378 | 12/1967 | Downs | 324/72 X |
| 3,443,224 | 5/1969 | Kramer et al. | 324/72.5 |
| 3,449,668 | 6/1969 | Blackwell et al. | 324/72 |
| 3,601,694 | 8/1971 | Checketts | 324/454 |
| 4,041,375 | 8/1977 | Polukhina et al. | 324/454 |
| 4,106,869 | 8/1978 | Buchheit | 324/72 X |
| 4,233,562 | 11/1980 | Blythe | 324/455 |
| 4,443,764 | 4/1984 | Suh et al. | 324/456 |
| 4,553,089 | 12/1985 | Lewiner et al. | 324/71.1 |

Primary Examiner—Gerard R. Strecker

[57] ABSTRACT

An electrical conductor is spaced close to an insulating web to detect electrostatic surface charges on the surface of the web.

11 Claims, 1 Drawing Sheet

ON-LINE ELECTROSTATIC DEFECT DETECTOR FOR POLYESTER BASE

BACKGROUND OF THE INVENTION

This invention relates to a method and apparatus for the nondestructive, on-line testing of webs and, more particularly to a method and apparatus for detecting the presence of surface defects on a running web having an electrostatic charge distributed thereon.

DESCRIPTION OF THE PRIOR ART

In the present sophisticated, high technology, competitive industrial environment there are numerous products and processes which involve coating one or more layers of various substances on a supporting web, typically a thin polymeric continuous sheet. Such products include, for instance, photosensitive film sheets useful in radiography which are produced in a continuous process comprising unwinding a web from a roll, typically a polyethylene terephthalate web, passing the web through a coating station, where one or more layers of photosensitive and inert, protective, coatings are placed on the web surface, drying it in a dryer section, and finally, winding it up in a roll prior to slitting and chopping to produce the familiar film sheets used in radiography. Similarly, coloring layers or layers sensitive to radiation, such as photopolymerizable or photo-crosslinkable layers useful in the production of printed circuit boards and the like, may be coated on webs.

In most applications where a high quality coating is required, it is important that the web surface be free from irregularities or defects, since such defects will usually disturb the uniformity of the coated layer. For instance, the presence of dust specks on the web surface is detrimental, since they can prevent the coating from properly adhering to the web. This can cause small uncoated spots or where coated, the coating can eventually fall off. Small sharp peaks and valleys on the web surface are similarly detrimental since they affect the continuity and thickness uniformity of the coated layer.

It is therefore desirable to be able to detect the presence of such web surface irregularities so that having determined their positions on the web, one may later discard those portions of the coated web containing such defects. The rejection typically is made on the basis of predetermined criteria signifying what constitutes an acceptable magnitude of defect or an acceptable number of defects of a given magnitude, based on past experience of required product quality level. Other criteria may be used as well. Many of the usual inspection techniques such as ultrasonics, radiography, thermal imaging, microwaves, holography, and acoustics are not suitable for on-line measurements.

When the web comprises an electrically insulating material, which is the case for most webs serving as a base for coating or other uses, it is known to use electrostatic techniques to monitor the web. Using such techniques, an electrostatic charge may be placed on the web and measurement of this charge may be used as an indicator of certain web properties. U.S. Pat. No. 4,443,764 for instance measures the charge remaining on a base (web) electrostatically charged to a high potential following a given time delay between charge application and measurement. Charge leakage occurs through the thickness of the web to a ground plate and a disturbance in the charge decay pattern is an indication of a defect in the web. To determine the residual charge pattern the web is moved at a constant velocity under an electrostatic probe. Mulitple probes may be used. The presence of any defects are revealed as peaks or valleys in the charge profile. Speeds up to 6.4 cm/sec. have been attained using this technique.

U.S. Pat. No. 3,443,224 teaches the structure needed to produce a high resolution electrostatic probe, akin to a stylus, which may be used to scan the surface of a solid body to determine a local electrostatic charge distribution on that surface. The surface to be measured, e.g., a plastic film, is positioned between a grounded plate and the probe. Finally, U.S. Pat. No. 4,233,562 describes an apparatus for monitoring web surface conductivity by inducing an electrostatic charge on a moving web and observing the transverse redistribution of the charge. A shrouded electrostatic probe is used.

None of the above devices can be readily adapted for use as a reliable, inexpensive, on-line test instrument to generate information on the quality of a running web, as measured by the presence of surface irregularities. These devices measure an electrostatic voltage which is a function of the dielectric structure of the web and in one case at least requires that the electrostatic charge be placed on the web. This tends to mask surface irregularities.

SUMMARY OF THE INVENTION

Many of these disadvantages are alleviated by the method and apparatus of this invention. According this invention, a method for detecting the presence of surface irregularities on an electrically insulating web is disclosed, the web having an electrostatic surface charge, comprising the steps of:

effecting relative movement between the web and a first electrical conductor positioned close to the surface of the web to induce a first electrical signal in the conductor, and detecting the high frequency components of the first signal which are indicative of the presence of a surface irregularity on the web. The surface charge of surface irregularities is increased by subjecting the surface of the web to an electrically grounded region during detection. By counting the sharp voltage spikes in the signal, the number of defects is determined.

A second electrical conductor is positioned close to the surface of the web and adjacent the first conductor to permit the moving web to induce a second electrical signal in the second conductor. The second conductor is angled relative to the first conductor so that the time interval between the defect signals in the first and second conductors varies as a function of the transverse location of the defect.

The method and apparatus are extremely simple, use the naturally occurring electrostatic surface voltage and permit the monitoring of surface irregularities at relatively high web speeds.

BRIEF DESCRIPTION OF THE DRAWINGS

This invention will now be described with reference to the accompanying drawings, in which.

DETAILED DESCRIPTION OF THE INVENTION

The invention will best to be understood with reference to the accompanying drawings in which similar numbers refer to similar elements in the various representations.

Figure 1:
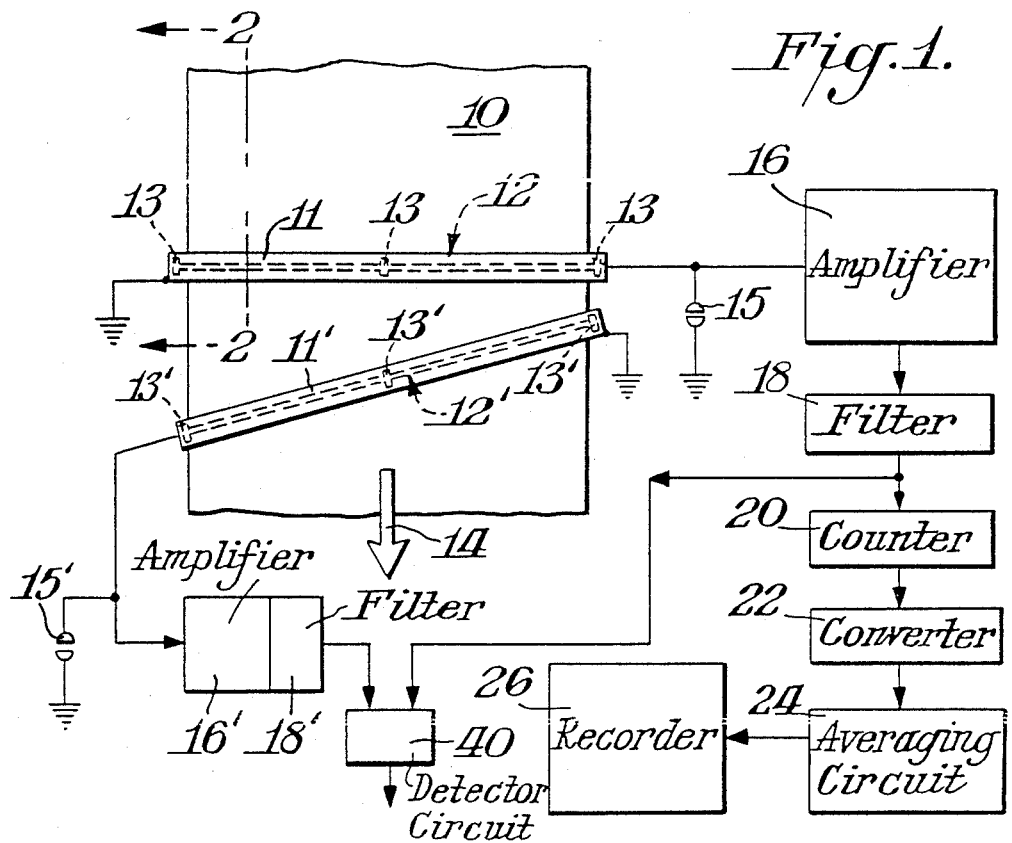
FIG. 1 represents a block diagram of the apparatus of this invention.
Figure 2:
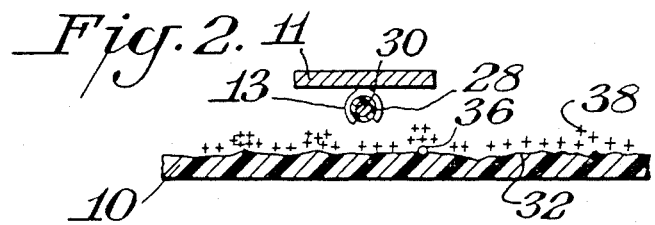
FIG. 2 is a cross-sectional elevation view taken along section line 2—2 of the apparatus of FIG. 1.

Referring now to FIG. 1, there is shown a web 10 moving in the direction of the arrow 14. The web may be formed of any electrically insulating material, but typically is a thin polymeric sheet which in the case of x-ray film base is polyethylene terephthalate. Supporting and driving means to transport web 10 past a number of stations where various operations to the web occur are conventional and for the sake of clarity not shown in this figure. The web is transported past a detector station, constructed in accordance with this invention, comprising an electrical conductor such as a wire 12 stretched transversely, preferrably perpendicularly, to the direction 14, across the width of the web 10. Preferably, as shown in FIG. 2, the wire 12 comprises a conductive core 30 surrounded by an insulating sleeve 28. The wire, which may be 20 gauge and teflon insulated, is supported across web 10 on a supporting plate 11 extending across the web 10, using a number of wire clip mounts 13, at a distance of about 0.6 cm from the web. The supporting plate 11 is mounted preferably rigidly on the same frame (not shown) which supports the transport means and the web 10. Plate 11 is electrically conductive and connected to a ground common to the rest of the electrical components forming this invention. The wire 12 may be located in a V-groove formed in the plate 11 for shielding purposes.

One end of wire 12 is connected to the input of a high input impedance amplifier 16, having an input impedance of the order of $10^7$ to $10^8$ ohms or higher. A Keithly electrometer amplifier may be used for this purpose. A gas discharge tube 15 such as a neon gas bulb is placed across the input of the amplifier to protect the amplifier against high voltage peaks on the wire 12.

To eliminate undesirable voltage fluctuation in the detected signal resulting from web flutter, 60 Hz hum or other low frequency sources of noise, a high pass filter 18 having a low end cutoff frequency of around 200 Hz is placed at the output of amplifier 16. This permits only sharp voltage changes, such as spikes representing dust and other imperfections, having a sharp point, on the web surface to pass.

The signal may now be displayed as is or may further be processed. In the preferred embodiment, the filtered output of the amplifier 16 drives a counter 20 which counts the sharp spikes. The counter 20, which includes a threshold detector that is adjustable to pass only counting pulses exceeding a predetermined amplitude may be purchased from Red Lion and the filter may be a Ithaco Dual Model 4302. The counter is a digital counter and includes reset means which permits the counter to count and hence integrate pulses, so as to provide output yielding pulses at each reset on a per second or per minute basis. Thus both the magnitude of the defect signal and the number of defects per unit length (area) of the moving web may be determined.

In the preferred embodiment, a digital to analog converter 22 provides 4 to 20 MA current output, corresponding to a count frequency of 0 to 100 counts per second, and may be used to drive a recorder 26. Again in the preferred embodiment, this signal is not used directly, but the integrated output of a number of cylces of counter output is averaged in an averaging circuit 24 to provide a signal driving the recorder 26 which represents a continuous average of the defects per second.

In addition to being a high pass filter with a 200 Hz cutoff point, filter 18 may be also include a pulse width discriminator circuit. In that instance, defects of a predetermined size may be detected by adjusting the pulse duration for pulses allowed to pass through the filter to equal the transit time of the defect under the wire 12. This time is readily derived from the speed of transport of the web 10 and the dimension of the defect in the web transport direction.

In an alternative embodiment, a second detector may be positioned, transverse to the direction of web movement 14, across the web to provide information locating the transverse position of a defect across the web in addition to its length. For this purpose, a second wire 12' mounted on a grounded plate 11' by mounting clips 13' is placed across the web 10, at an angle relative to the first wire 12. Both wires are the same and maintained in a plane parallel to the web plane. The output signal of this second wire 12' is also directed through a neon gas lamp protective circuit 15' to a high impedance amplifier 16' (the same as amplifier 16) the output of which is directed to a high pass filter 18' having substantially identical characteristics as filter 18. Here also the second wire 12' is positioned between the plate and the web.

The outputs of filters 18 and 18' are directed to a phase detector circuit 40 which comprises a threshold detector and preferably pulse shaping circuitry such as a multivibrator type circuit. The output of phase detector 40 may be observed in an oscilloscope or may be directed to other instruments albe to measure the time difference between the leading edge of the two sequential pulses. This time difference is recorded. Since the geometry of the positioning of the two wires is known, as well as the speed of transport of the web, the time difference between the leading edges of the pulses generated by the leading edge of a defect in wires 12 and 12' is proportional to the distance between the wires. Since the wires are angled relative to each other, this distance varies from one end of the web width to the other, and uniquely defines the position of the leading edge of the defect across the web width. Such determination may be done using a computer.

In operation, during the winding and unwinding process, a web, particularly a polymeric, insulating web, accummulates a mechanically induced electrostatic charge on its surface 32 as shown in FIG. 2 by numeral 38. As shown in that figure, the web surface is not optically flat, but contains numerous peaks and valleys, within the manufacturing smoothness specifications. Occasionally there are defects which are in the form of higher peaks 36. In the alternative, small dust specks may be attracted to the surface. Charges tend to concentrate on these high points, seeking to leak off, much in the manner that charges concentrate at the tips of sailboat masts in stormy weather producing the once puzzling halo effect known as St. Elmo's fire. The plate 11 helps facilitate this leakage and shields the wire 12 from extraneous noise. By facilitating the leakage, the electrostatic charge concentration on the high points is increased.

As the web is unwound and driven past the detector, the background relatively uniform or slowly changing electrostatic charge distribution produces a relatively uniform or slowly changing field across the wire 12.

When the field is not changing, there is little or no current flow induced in the wire. However as the higher charge on a dust speck or peck asperity on the base 10 passes at high speed under the wire 12, the monetary electric field fluctuation induces a sharp current pulse or spike in the wire which is amplified and counted by the circuitry described above. Thus even though the difference in electrostatic potential between background and an asperity peak is very small, when one tries to read it over the background potential, the pulse generated in the wires is clearly detectable as it is essentially the only current produce. The sharp spike is made up of higher frequency components which can pass through the filters 18, 18'. They may be phase compared to establish the lateral position of the asperity across the web. The signal from amplifier 16 may be processed further, as described and displayed on the recorder 26.

Figure 3:
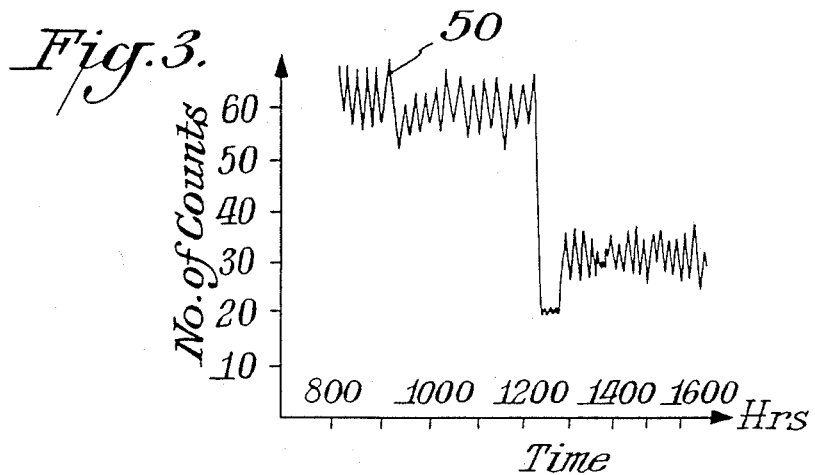
FIG. 3 shows a typical curve displaying the output of the apparatus of FIG. 1.

A typical waveform displayed on the recorder 26 representing the output of the defect detector used to monitor a web line is depicted in FIG. 3. The high level of the waveform 50 indicates a significant number of defects either in the surface of the web or in the web drive system which when corrected results in a much lower level waveform as may be seen in FIG. 3, at 0800 on a particular day the counts per unit time was relatively high. After the defects in the line were corrected (around 1300 hours, the count dropped to a lower level indicating satisfactory operation.

In an alternative embodiment, a conventional source of ionized air (not shown) may be passed across the web in the gap between the plate and the web. This enhances the ability of the plate 11 to discharge the web surface which reduces background noise.

The above description of this invention discloses a complete apparatus having a number of refinements directed to particular applications, and as such should not be considered as limiting but simply illustrative. Those having the benefit of the above description will readily recognize that additional elements may be added to further process the signal output from wire 12 to obtain the same or similar data. Similarly, certain elements present in the above description may also be omitted depending on the final result sought. Computer signal processing may be substituted for some of the discreet components; these and similar modifications are well within the scope of the invention.

I claim:

1. A method for detecting the presence of surface irregularities on an electrically insulating web, the web having an electrostatic surface charge and an electrostatic field associated therewith, comprising the steps of:
    effecting relative movement between the web and a first electrical conductor positioned across and close to the surface of the web to induce in the conductor a first electrical signal corresponding to electrostatic field variations resulting from the distribution of the electrostatic surface charge on the web and from the relative movement of the web and the first electrical conductor, and
    detecting the sharp voltage changes having frequency components from about 200 Hz and above of the first signal which are indicative of the presence of a surface irregularity on the web.

2. A method as set forth in claim 1 which includes the additional step of increasing the magnitude of the electrostatic field in the vicinity of the first electrical conductor by providing an electrically grounded region co-extensive with the conductor length, extending behind and on either side thereof and electrically insulated therefrom during detection.

3. A method as set forth in claim 2 which includes the additional step of counting only the detected components of the signal over a predetermined period of time, the count being indicative of the number defects per lineal length of the web.

4. A method as set forth in claim 1 which includes the additional step of counting only the sharp amplitude changes having frequency components greater than 200 Hz in the signal over a predetermined period of time, the count being indicative of the number of defects of a preselected magnitude per linear length of the web.

5. A method as set forth in claim 1 which includes the additional step of:
    positioning a second electrical conductor close to the surface of the web and adjacent the first conductor to induce in the second conductor a second electrical signal also corresponding to electrostatic field variations resulting from the distribution of the electrostatic surface charge on the web and from the relative movement between the web and the second electrical conductor,
    positioning the second conductor relative to the first conductor so that the time interval between when the first and second signals occur for a given surface irregularity varies as a function of the given irregularity's traverse location relative to the direction of relative movement,
    detecting the sharp voltage changes having frequency components from about 200 Hz and above of the second signal which are indicative of the presence of a surface irregularity on the web, and
    measuring the time interval between the first and second signals to determine the transverse location of a surface irregularity.

6. A method as set forth in claim 5 which includes the additional step of counting only the detected components in the signal over a predetermined period of time, the count being indicative of the number defects per lineal length of the web.

7. A method as set forth in claim 1 which includes the additional step of passing ionized air into the region between the first electrical conductor and web.

8. A method as set forth in claim 2 which includes the additional step of passing ionized air into the region between the first electrical conductor and web.

9. A method as set forth in claim 5 which includes the additional step of passing ionized air into the region between the first and second conductors and the web.

10. A device for detecting the presence of surface irregularities in a dielectric web, the web having an electrical surface charge, and an electrostatic field associated therewith, comprising:
    a first electrical conductor positioned close to the surface of the web and extending across the width of the web,
    means for effecting relative movement between the first conductor and the web along the length of the web, thereby to induce in the first conductor a first electrical signal corresponding to electrostatic field variations resulting from the distribution of the electrostatic surface charge on the web and from relative movement of the web and the first electrical conductor, a detector responsive to the first electrical signal for detecting sharp amplitude changes having frequency components from about 200 Hz and above of the signal which are indicative of the presence of a surface irregularity in the web, and a plate, electrically grounded, positioned adjacent to the surface of the web and extending the full width of the web with the first conductor therebetween.

11. A device as set forth in claim 10 which includes a second electrical conductor positioned adjacent the first conductor close to the surface of the web but angled with respect to the first conductor, the detector being responsive to the detected components of the second signal, and means for measuring the time interval between the detected components corresponding to the first and second signals, which time interval is related to the transverse location of a surface irregularity.

* * * * *